United States Patent [19]

Schmidtberger

[11] Patent Number: 4,565,652
[45] Date of Patent: Jan. 21, 1986

[54] PROCESS FOR REMOVING LIPOPROTEINS USING DERIVATIZED POLYHYDROXYMETHYLENE

[75] Inventor: Rudolf Schmidtberger, Marburg, Fed. Rep. of Germany

[73] Assignee: Behringwerke Aktiengesellschaft, Marburg, Fed. Rep. of Germany

[21] Appl. No.: 643,465

[22] Filed: Aug. 23, 1984

[30] Foreign Application Priority Data

Aug. 25, 1983 [DE] Fed. Rep. of Germany ....... 3330648

[51] Int. Cl.$^4$ .................... C07G 7/00; G01N 33/92
[52] U.S. Cl. ......................... 260/112 B; 260/112 R; 424/101
[58] Field of Search .................... 260/112 B, 112 R; 424/101

[56] References Cited

U.S. PATENT DOCUMENTS

| | | | |
|---|---|---|---|
| 3,955,925 | 5/1976 | Proksch et al. | 260/112 B X |
| 4,096,136 | 6/1978 | Ayers et al. | 260/112 B |
| 4,098,771 | 7/1978 | Huemer et al. | 526/269 X |
| 4,110,077 | 8/1978 | Klein et al. | 260/112 B X |
| 4,290,774 | 9/1981 | Girgis et al. | 260/112 B X |
| 4,309,188 | 1/1982 | Bentzen | 260/112 B X |
| 4,473,553 | 9/1984 | Zuffi et al. | 424/101 |

*Primary Examiner*—Howard E. Schain
*Attorney, Agent, or Firm*—Finnegan, Henderson, Farabow, Garrett & Dunner

[57] ABSTRACT

A process for binding and removing lipoproteins from aqueous fluids is described, the lipoproteins being bound to polyhydroxymethylene, onto which is grafted an oxyethylated alcohol or an oxyethylated carboxylic acid, and, where appropriate, being eluted from the polyhydroxymethylene. The process is also suitable for blood plasma or serum.

4 Claims, No Drawings

PROCESS FOR REMOVING LIPOPROTEINS USING DERIVATIZED POLYHYDROXYMETHYLENE

The invention relates to a process for removing lipoproteins from aqueous fluids by binding to polyhydroxymethylene onto which has been grafted an oxyethylated alcohol or an oxyethylated carboxylic acid.

It has proved to be advantageous in the processing of storable plasma and sera from human or animal blood for therapeutic or diagnostic purposes to remove all labile proteins unless they are necessary for the intended use. Lipoproteins are among the constituents of plasma and serum which have particularly adverse effects on the storability of the abovementioned solutions.

Lipoproteins are the water-soluble form for transporting triglycerides, cholesterol esters and phospholipids in biological fluids. They derive their solubility in water from protein moieties which surround, in the manner of a sheath, the lipids which are intrinsically insoluble in water. In the extreme case, the proportion of protein in the lipoprotein can amount to only a few percent. Moreover, the large and variable proportion of lipids which are insoluble in water is the cause of their stability in solution being less than that of proteins and glycoproteins. However, this stability in solution is an indispensable prerequisite for the use of biological fluids, such as, for example, plasma or sera, for both therapeutic and diagnostic applications. Thus, there has been no lack of attempts to remove lipoproteins from plasma or sera without changing the biological activities which are important to the user. This change can take the form of, for example, a reduction in the antibody content of an antiserum or of undesired activation of a coagulation factor.

Three methods for removing lipoproteins from biological fluids, such as plasma or serum, are available by the state of the art, as follows:

The method of flotation of the lipoproteins when the density is increased requires the use of high-speed centrifuges. The removal of all lipoproteins from serum requires the density to be increased to 1.21, and this is generally brought about by adding potassium bromide. The necessity for returning the non-lipoproteins to a physiological medium before their therapeutic use is another hindrance to this technique being transferred to large volumes.

Many adsorbents for adsorbing the lipoproteins onto selectively binding adsorbents have been described, and their common characteristic is a hydrophilic matrix, which is in the form of beads and is based on polysaccharides, to which phenyl or alkyl groups are bonded. Undesired interactions with components in the biological solutions, such as fibrinogen, and the fact that they can be attacked by enzymes are disadvantages. Adsorbents binding lipoproteins also include those based on silicon dioxide. These silicon dioxides, which are commercially available under the name Aerosil$^R$, can only be used in stirred processes, but inclusion in the sediment of liquid containing dissolved substances also takes place. It is true that the latter can be recovered in a washing procedure, but they then result in a diluted form which cannot be used. A further disadvantage of the silicon dioxide adsorbents is their noticeable solubility at pH values of 7 and above. In addition, their selectivity is inadequate in many cases so that, for example, it is impossible to remove lipoproteins from human or animal plasma while retaining their coagulation properties.

Furthermore, it has been disclosed that lipoproteins can be precipitated with polyanions, such as dextran sulfate or heparin. Cations such as $Mg^{++}$ or $Mn^{++}$ must be present during this. The quantities of polyanions and metal ions remaining in the supernatant then have to be removed.

For these reasons, it has been impossible to remove lipoproteins from plasma or sera of human or animal origin on the 100-liter scale where the intention was to avoid a change in the electrolyte ratios and the pH, a dilution of the plasma or serum, the danger of introducing substances leading to intolerance on therapeutic use, such as bacterial pyrogens, and changes in the ratios of the amounts of the proteins remaining in the solution. In addition, it ought to be possible to use the process under sterile conditions.

Thus the invention had the object of finding a process for removing lipoproteins from aqueous fluids which fulfils these conditions.

It has been found, surprisingly, that polyhydroxymethylene which is insolbule in water and onto which an oxyethylated alcohol or an oxyethylated aliphatic carboxylic acid has been grafted is capable of binding lipoproteins in aqueous fluids.

Thus the invention relates to a process for removing lipoproteins from an aqueous fluid, which process comprises bringing the fluid into contact with a polyhydroxymethylene onto which has been grafted an oxyethylated alcohol or an oxyethylated carboxylic acid. The following are preferred: an alkanol having 4 to 30 carbon atoms as the alcohol or an aliphatic carboxylic acid having 4 to 20 carbon atoms. A derivatized polyhydroxymethylene (PHM) of this type can be prepared by a method in German Offenlegungsschrift 2,556,759 (U.S. Pat. No. 4,098,771). A PHM which has been prepared by the methods in the examples in this patent is particularly suitable. From 1 to 20, preferably 2 to 10, percent by weight of an oxyethylated alcohol or an oxyethylated carboxylic acid is employed in the polymerization. The particular advantages of a polymer of this type derive from a number of properties of the material by which it differs from other known adsorbents. Polyhydroxymethylene is a synthetic polymer in which the chain is exclusively carbon and in which, in a preferred embodiment of the preparation, alkyl groups are incorporated via ether bonds. Thus the final product only contains types of bonds which are known to have not only high chemical and thermal stability but also good enzymatic stability. Since it lacks ionic groups, polyhydroxymethylene is incapable of undesired ionic interactions. The OH groups which are linked to each of the carbon atoms in the polyhydroxymethylene ensure high wettability of the adsorbent with aqueous solutions, and this has an advantageous effect in the retention of the natural structures of proteins whose solutions are treated with it. Utilizing its stability to alkali, polyhydroxymethylene derivatized with an oxyethylated alcohol can be treated with hot alkali metal hydroxide solution and, after it has been neutralized, this can be followed by sterile and pyrogen-free use. The possibility of carrying out a measure of this type is of great importance in the context of working up protein solutions for therapeutic use. Although polyhydroxymethylene derivatized as specified in the claim is able to bind lipoproteins from solutions within a wide pH range and having various types and concentrations of electrolytes, it is a particular advantage that it also exhibits this property at physiological salt and pH conditions when applied to plasma and sera. Thus it is unnecessary to change the reaction conditions beforehand and to reverse this after the adsorption step.

The lipoproteins can be bound either in a stirred process or using a column technique. The polyhydroxymethylene can be used in the hydrated or freeze-dried form. In the latter case, it is possible to provide the adsorbent with a particular shape by compression. It is advantageous to obtain the polyvinylene carbonate, from which the PHM is prepared by hydrolysis, by polymerization in the presence of dispersants by the method in German Patent Application 3,243,591. The fact that the derivatized polyhydroxymethylene is precipitated from an alkaline solution makes it possible to carry out the precipitation in the presence of finely divided particles. These undergo inclusion in the precipitating polyhydroxymethylene and can thus confer on the coprecipitate properties which facilitate, or in fact alone make possible, subsequent use. Thus, inclusion of particles of magnetite can confer susceptibility to magnetic effects. It is possible, for example, by inclusion of kieselguhr to improve the flow characteristics of polyhydroxymethylene column packings. The inclusion of carbon particles can give rise to additional adsorption effects.

If the intention is to obtain the lipoproteins which are bound to the polyhydroxymethylene, there is a choice for this purpose of all eluting agents known to dissociate hydrophobic binding.

The example which follows illustrates the invention.

EXAMPLE 200 g of polyvinylene carbonate, prepared by the method of U.S. Pat. No. 4,098,771, were suspended in 3,000 ml of 5 M NaOH in a stainless steel vessel. The suspension was heated, with stirring, up to 90° C. in 30 minutes. The polymer completely dissolved during this. Then the solution, while still hot, was diluted with 40 liters of water while stirring. The polyhydroxymethylene which is insoluble in water separated out during this as an amorphous precipitate. 400 g of solid NaCl were added to the suspension to speed up this precipitation. After three hours, most of the liquid over the precipitate was siphoned off. 10 molar HCl was added, with stirring, to the part of the mixture remaining in the container until the suspension reached a pH of 12. The solid and liquid were separated by filtration, and residual alkali was washed out of the residue on the filter using 0.15 molar NaCl solution. The product thus obtained was stirred with 0.15 molar NaCl solution to form a suspension, and the pH of this was adjusted to 7.5 with 1 molar HCl and the volume was made up to 3 liters.

11 g of trisodium citrate were dissolved, with stirring, in this suspension of the polyhydroxymethylene derivative. Then a chromatography column of diameter 19 cm was packed with this suspension. 27 $\mu$g of hepatitis B s antigen were added to 1.4 liters of human plasma, which had been obtained with citrate ions as the complexing agent, and the mixture was allowed to run through the column. The fractions eluting off the column with the highest concentrations of protein were combined; they had a total volume 1.6 liters and contained 89% of the proteins in the initial plasma. In the plasma thus treated, it was impossible to detect, using known methods, cholesterol (CHOD-PAP method), or apo-B protein (turbidimetric immune reaction) or HBsAg (ELISA technique).

I claim:

1. A process for removing lipoproteins from an aqueous fluid, which comprises bringing said fluid into contact with a polyhydroxymethylene onto which has been grafted an oxyethylated alcohol or an oxyethylated carboxylic acid and separating the fluid from said polyhydroxymethylene to which at least some of said lipoproteins have become bound.

2. The process as claimed in claim 1, wherein the alcohol is an alkanol having 4 to 30 carbon atoms, or the carboxylic acid is an aliphatic carboxylic acid having 4 to 20 carbon atoms.

3. The process as claimed in claim 1, wherein the fluid is blood plasma or serum.

4. A process for removing virtually all lipoprotein from an aqueous plasma or serum, which comprises bring said plasma or serum into contact with a polyhydroxymethylene onto which has been grafted an oxethylated alcohol or an oxethylated carboxylic acid and separating the plasma or serum from said polyhdroxymethylene to which virtually all of said lipoprotein has become bound.

* * * * *